United States Patent [19]

Farquhar et al.

[11] Patent Number: 5,525,915
[45] Date of Patent: Jun. 11, 1996

[54] ELECTRICAL CONDUCTIVITY TESTER FOR ROPES

[75] Inventors: John A. Farquhar, Vancouver; Gary Lecomte, New Westminster, both of Canada

[73] Assignee: Hi-Test Detection Instruments Ltd., Vancouver B.C., Canada

[21] Appl. No.: 379,924

[22] Filed: Jan. 27, 1995

[51] Int. Cl.⁶ .......................... G01R 31/08; G01R 31/12
[52] U.S. Cl. .......................... 324/558; 324/515; 324/701; 324/724; 340/677
[58] Field of Search .................... 324/513, 515, 324/516, 517, 518, 558, 557, 722, 724, 701; 340/677

[56] References Cited

U.S. PATENT DOCUMENTS

| | | | |
|---|---|---|---|
| 2,471,560 | 5/1949 | Everson | 324/515 |
| 3,343,081 | 9/1967 | Lang | 324/558 |
| 3,364,420 | 1/1968 | Kreuger | 324/513 |
| 4,446,422 | 5/1984 | Koehler | 324/515 |
| 5,302,904 | 4/1994 | Nopper | 324/515 |

*Primary Examiner*—Kenneth A. Wieder
*Assistant Examiner*—Jose M. Solis
*Attorney, Agent, or Firm*—Adrian Zahl

[57] ABSTRACT

A tester is provided for measuring the dielectric integrity of a rope, on a continuous basis. The device incorporates a pair of rope contact and retention members, that may comprise pair of spring-loaded clamps, adapted to make electrical contact with the rope, while permitting the rope to be drawn longitudinally through the device. The contact or retention members may either be adapted to make a sliding contact with the rope or may employ wheels or roller members to facilitate the movement of the rope through the device. The contact members are linked to an electrical testing circuit for measuring the conductivity of the rope segment under test. The contact and retention members may also comprise an iris having an array of flexible leaves extending inwardly from an annular retainer, with the leaves being linked to the testing circuit and adapted to press against a rope inserted within the retainer. Some or all of the leaves are connected to the testing circuit.

14 Claims, 10 Drawing Sheets

ELECTRICAL CONDUCTIVITY TESTER FOR ROPES

FIELD OF THE INVENTION

The present invention relates to an apparatus for use by workers engaged in repairing high voltage electrical cables, to enable them to test the electrical conductivity of ropes in order to assess their dielectric integrity.

BACKGROUND OF THE INVENTION

Repair work conducted on high voltage electrical cables is typically conducted while current flows through the cables. Consequently, it is imperative that workers in contact with cables and crews on the ground remain at all times electrically isolated. In order to transfer objects from a crew on the ground to a worker in the air, non-conductive ropes are employed to ensure that the aerial worker is not electrically grounded and the ground crew is not in electrical contact with the cable. When ropes made of a resistive material such as hemp or nylon are in clean and new condition, they remain largely non-conductive. However, as such ropes become soiled, they can become dangerously conductive. Accordingly, it is necessary to periodically test the dielectric integrity of ropes in use by workers, to ensure that they remain safely non-conductive.

It will be understood that the term "rope" as used herein refers as well to straps, cords, and the like. It will be further understood that although reference is generally made herein to testers adapted to measure conductivity, with slight adaptations they may be used to measure resistivity.

Dielectric rope testers typically make electrical contact with a rope under test at two points a fixed distance apart, and measure the conductivity of the rope between the points. Such devices must grasp the rope tightly enough to make electrical contact at the two points. However, they should also permit the entire length of the rope, or a reasonable portion thereof, to be passed relatively quickly and easily through the device. Previous such devices have lacked a means to make secure electrical contact with a rope being passed through the device. Typically, such devices are provided with a pair of contacts, with the rope being simply placed on the contacts. The user has to ensure that the rope is making electrical contact with both contacts, and this can be a time-consuming operation when a long rope is being tested. As well, the user cannot be certain that the rope has in fact been properly tested, since there is no way of ensuring that the contacts have in fact contacted the rope.

In order to achieve reasonable ease of use and certainty of testing with a testing device, the device should be capable of easily and securely engaging and disengaging a rope under test. As well, it should be possible to pull the rope through the device continuously, with the conductivity of the segment of rope under test being measured on a continuous basis between the contacts.

Accordingly, it is an object of the present invention to provide a rope testing device that accurately measures the conductivity of a rope between two spaced-apart probes, wherein the probes are capable of easy and secure engagement to the rope, while permitting the rope to be pulled through the device continuously.

SUMMARY OF THE INVENTION

The present invention comprises a tester for measuring the dielectric integrity of a rope, adapted to achieve the objects set out above. In order to permit a rope to be tested on a continuous basis, the device is provided with a probe means adapted to clampingly engage and electrically contact the rope while permitting the rope to be drawn longitudinally through the device. The probe means is mounted to a base, which may also house the conductivity testing circuit. The probe means consists of first and second parts, the first part consisting of a pair of rope contact members that make electrical contact with a segment of rope under test at two spaced-apart positions along the segment. The rope is pressed against the contact members by one or more rope retention members that are spring-biased towards the contact members. In one embodiment, the contact members each comprise indented plates or shoes, with the indentation shaped to maximize the contact area of the rope and to hold the rope in position during the testing operation. The contact or retention members may either be adapted to make a sliding contact with the rope or may employ wheels or roller members to facilitate the movement of the rope through the device. As well, the retention members can themselves be incorporated into the electrical circuit, to maximize the electrical contact with the rope.

The rope contact and retention members may comprise two sets of upper and lower opposing jaws, respectively, spaced apart from each other and with the lower jaw being mounted to the base and the upper jaw being hinged to the lower jaw and spring-biased towards the lower jaw. The jaws slideably engage a rope that may be drawn through the device. The upper and lower jaws may each be provided with a recessed portion shaped to maximize their contact area with the rope as the rope is drawn through the jaws. As well, both upper and both lower jaws may be respectively retained within upper and lower retainers, hinged at one end and mounted to the base.

Alternatively, the rope retention member may comprise a single spring-loaded plate positioned midway between the contact members.

The contact and retention members may also comprise an iris having an array of flexible leaves extending inwardly from an annular retainer, with the leaves being linked to the testing circuit and adapted to press against a rope inserted within the retainer. Some or all of the leaves are connected to the testing circuit.

The electrical circuit comprises in its broadest form: a power source electrically linked to one of the rope contact members; a metering circuit adapted to measure conductivity or resistivity, linked to a second of the contact members; and indicator means to indicate the conductivity or resistivity of the rope segment under test.

In a preferred embodiment of the invention, the power source comprises a battery linked to a transformer circuit adapted to boost the current to between 9,000 and 11,000 volts, with the rope contact members being positioned about four inches apart on the base. Other combinations of voltages and distances are possible.

The indicator means may comprise visual and/or audible indicators.

DETAILED DESCRIPTION OF THE PREFERRED EMBODIMENTS

The rope tester of the preferred embodiments is provided with a case within which the electronic components are housed, with a probe means being mounted externally to the case. The probe means comprises in its broadest aspect two rope contact members, spaced apart from each other and each adapted to contact a rope under test at two spaced apart points along the rope, and one or more rope retention members adapted to press the rope against the contact members. In the preferred embodiments, a sliding contact means is provided wherein the rope simply slides between the contact and retention members. The contact and retention members may comprise discrete members, or may be incorporated into an iris-type design wherein the members comprise flexible leaves extending inwardly from an annular retainer. An alternative design provides one or more roller members or wheels incorporated into one or both of the contact or retention members, to permit a rolling contact with the rope as the rope is drawn through the device. The contact members are linked to a testing circuit, with the rope being placed between the contact members to complete the circuit.

Figure 1:
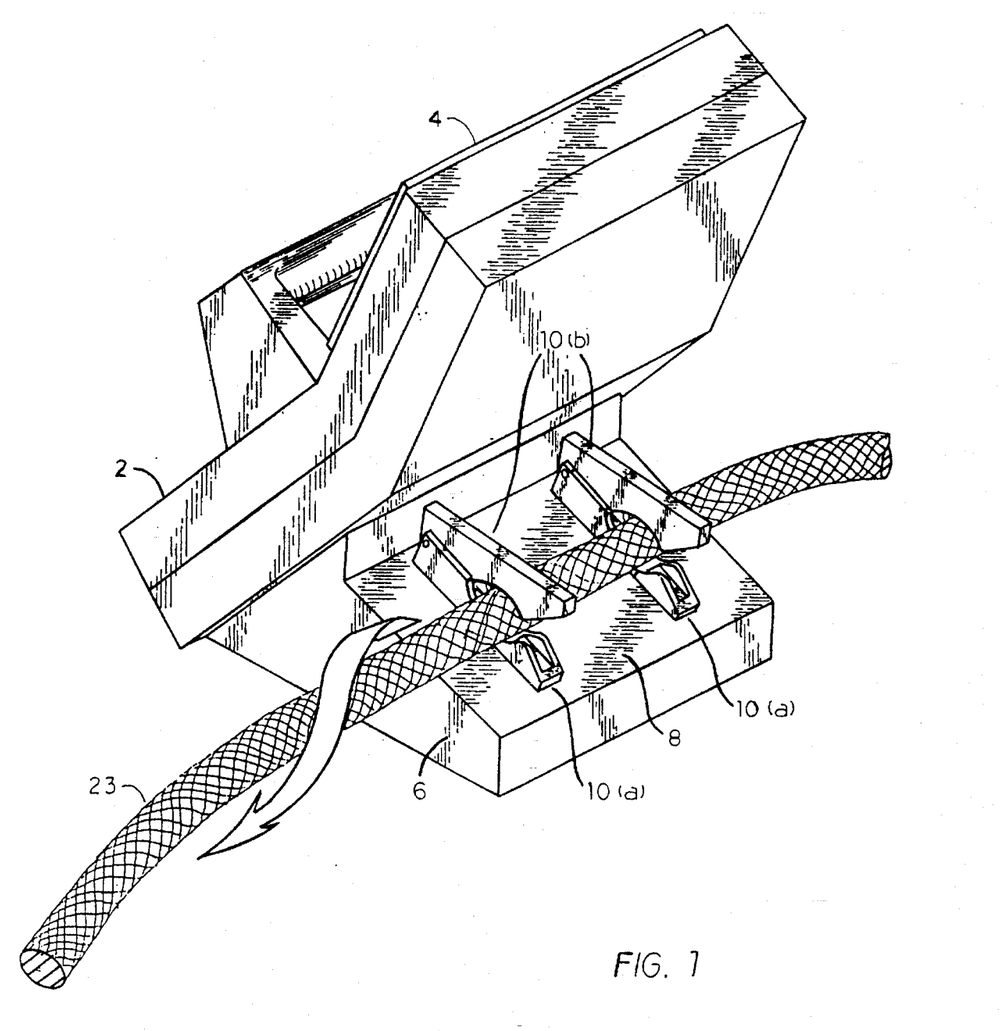
FIG. 1 is a perspective view of a first embodiment of the testing device according to the present invention, with a rope being grasped by the device in position for testing.

In a first embodiment of the device, illustrated in FIGS. 1–12, the probe means comprises two pairs of jaws 10 spaced apart from each other by about four inches, with a lower jaw member 10(a) of each pair comprising the rope contact member and an upper jaw member 10(b) comprising a retention member. As seen in FIG. 1, the case 2 consists of an upwardly tilting display portion 4, with a base 6 extending generally horizontally outwardly from the base of the case. The base 6 has an upper face 8, with the jaws 10 being mounted to the upper face 8.

Figure 2:
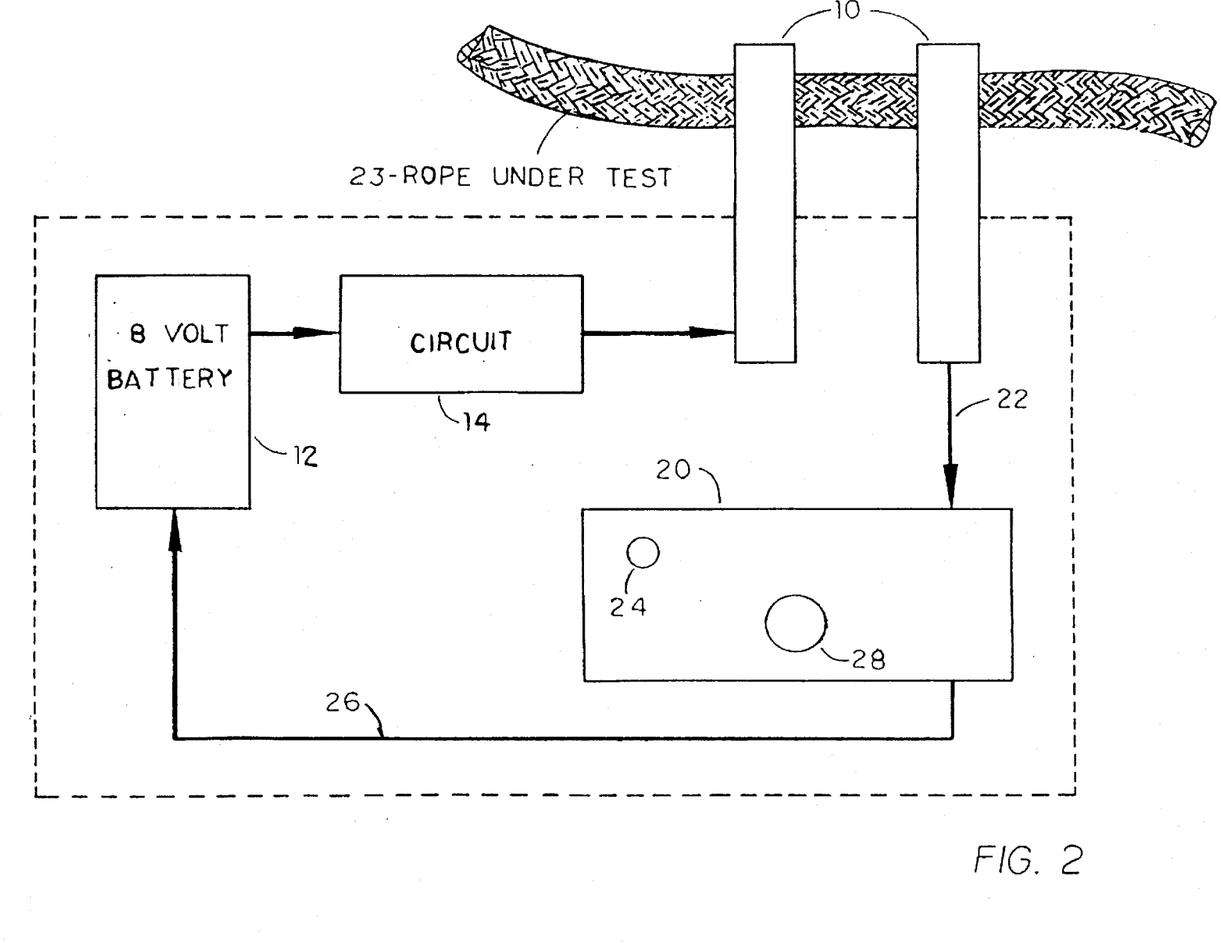
FIG. 2 is a schematic diagram of the electronic circuit of the device.
Figure 3:
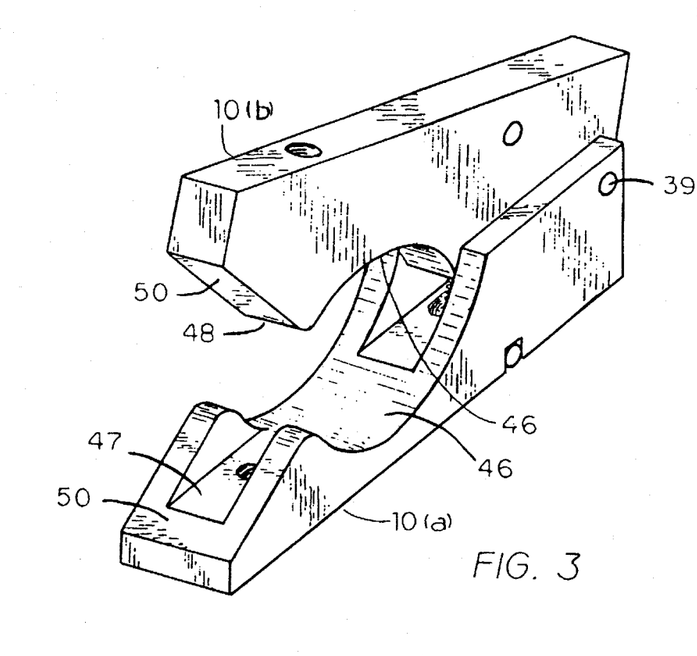
FIG. 3 is a perspective view of a portion of the probe means of the device, showing the jaws thereof in the open position.
Figure 4:
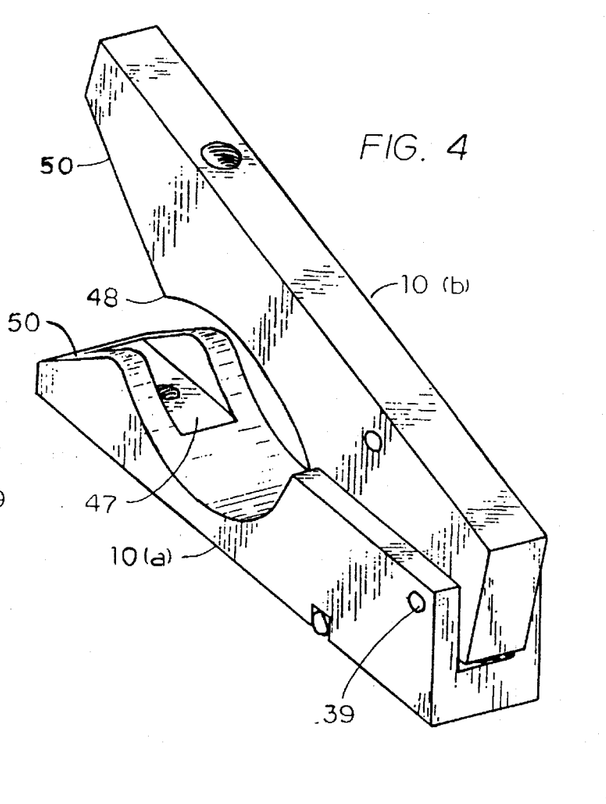
FIG. 4 is a second perspective view as in FIG. 3.
Figure 5:
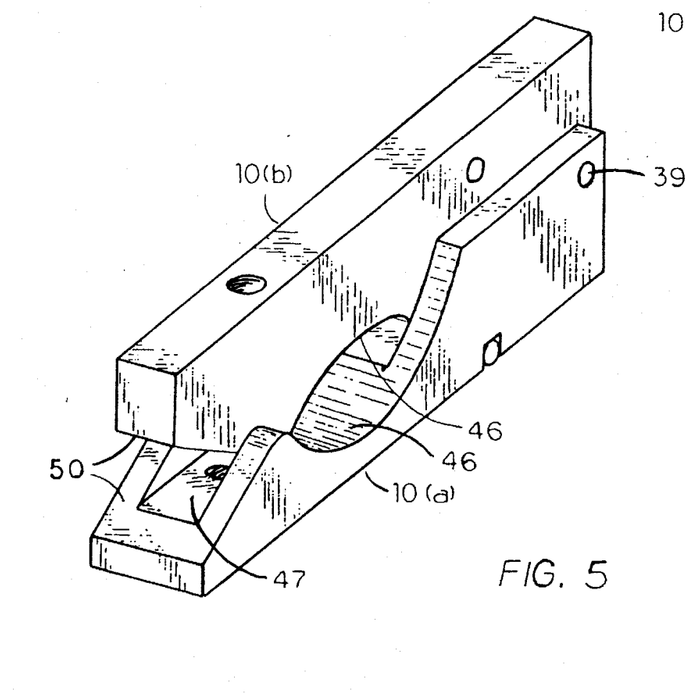
FIG. 5 is a perspective view of the jaws of the probe means in the closed position.
Figure 6:
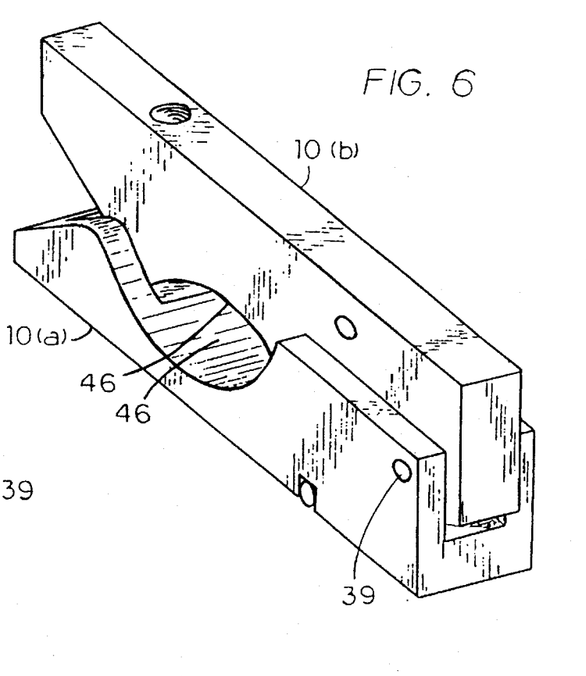
FIG. 6 is a second perspective view as in FIG. 5.
Figure 7:
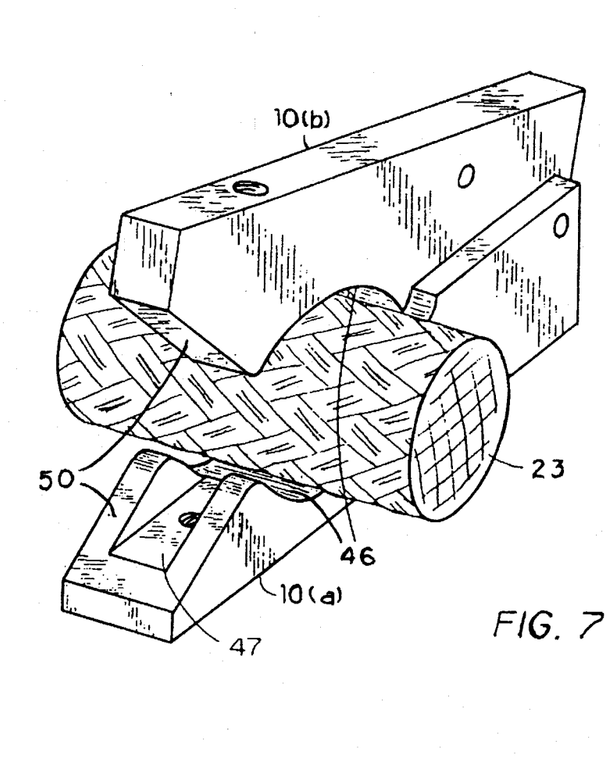
FIG. 7 is a perspective view of the jaws with a rope being gripped therebetween.
Figure 8:
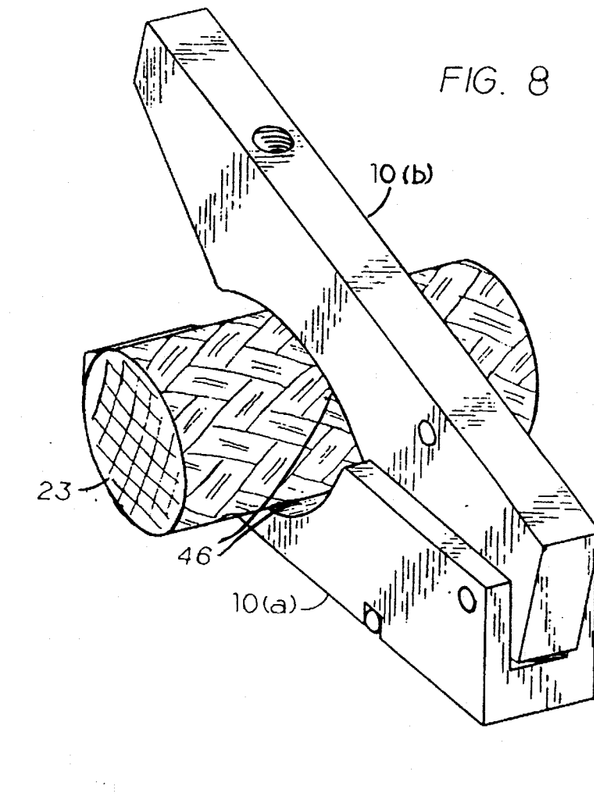
FIG. 8 is a second perspective view as in FIG. 7.
Figure 9:
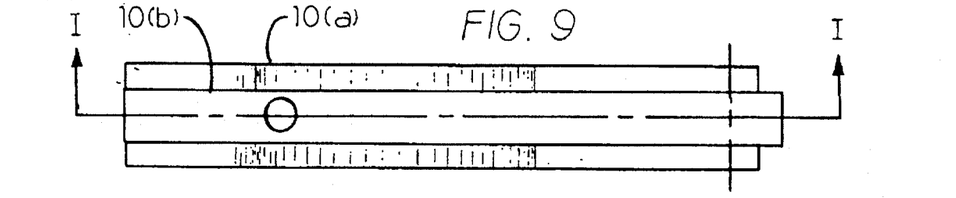
FIG. 9 is an upper plan view of the jaws.
Figure 10:
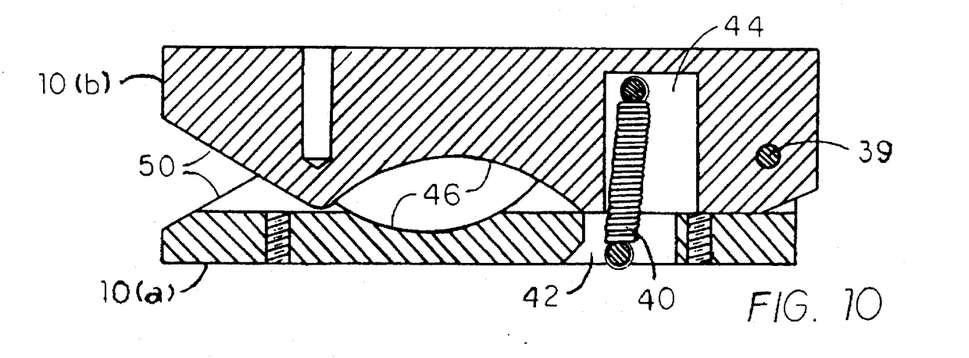
FIG. 10 is sectional view, along line I—I of FIG. 9.
Figure 11:
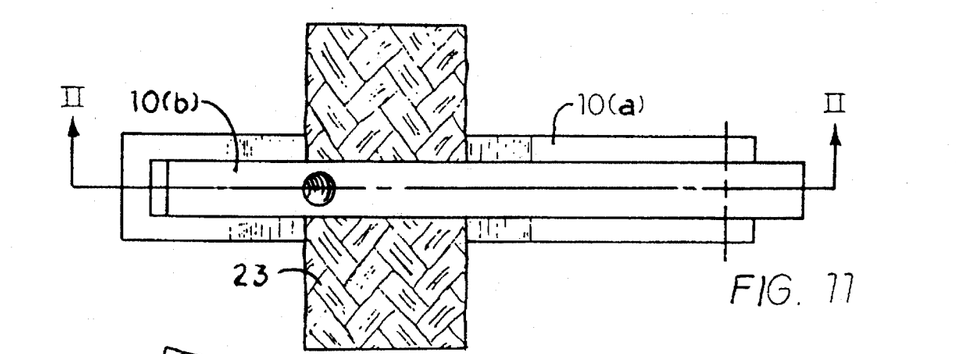
FIG. 11 is an upper plan view of the jaws, with a rope being gripped therebetween.
Figure 12:
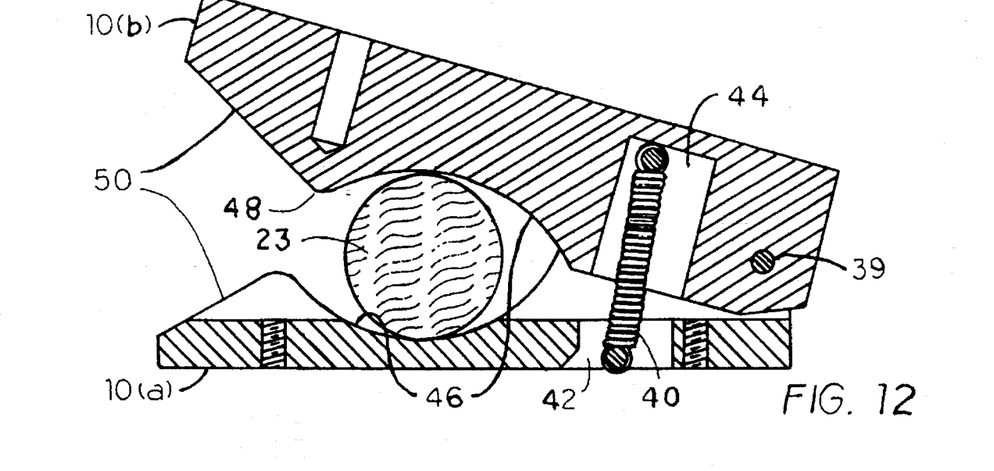
FIG. 12 is a sectional view, along line II—II of FIG. 11.

Within the case 2 is housed a conductivity measuring circuit, shown schematically in FIG. 2. A power source 12, comprising an 8 volt battery, is linked to a transforming circuit 14, which boosts the voltage within the circuit to between 9,000 and 11,000, and preferably about 10,000 volts. This current is connected to a first of the sets of lower and upper jaw members 10(a) and (b). The second set of lower and upper jaw members 10(a) and (b) is connected to a conductivity metering circuit 20 through a lead 22, and then to the battery by lead 26. The metering circuit 20 is linked to indicator means to signal the user in the event that the conductivity of the rope being tested exceeds a predetermined level, nominally 5 microamps, and the rope is bad. The indicator means comprises a light emitting diode ("LED") 24 which is illuminated when the conductivity exceeds the predetermined level. An audible indicator 28 may also be used to deliver an audible signal at the same time the LED lights. Alternatively or in addition, a standard pivoting needle-type current meter may be provided for a visual analog indication of the conductivity of the rope segment under test.

Referring to FIGS. 3–12, the lower and upper jaw members 10(a) and (b) are hinged together by means of a pivot pin 39. The jaws are fabricated from stainless steel, a material that provides an electrical connection with the rope 23 and minimizes the deposition of a conductive contaminant onto the rope while it is being pulled through the jaws. The lower jaws 10(a) are both mounted to the upper face 8 of the base 6 of the case. A spring 40, seen in FIGS. 10 and 12, biases the upper jaw downwardly towards the lower jaw, to permit the jaws to grip a rope firmly therebetween. The spring is retained within a pair of recesses 42 and 44 within the lower and upper jaws, respectively. The upper and lower jaws are both provided with opposing curved indentations 46, recessed into the lower and upper faces thereof, respectively. The indentations are shaped to cooperate with each other to retain a rope under test. The forward end of the lower jaw 10(a) terminates in a slotted portion 47, adapted to mate with a tongue 48 extending downwardly from the upper jaw 10(b). This feature permits the jaws to fold tightly together when not in use, and provides a decreasing effective radius of the respective jaws as they are brought together, in order to maximize the contact area as the device is used with ropes of varying thicknesses.

The outer ends 50 of the jaw members 10(a) and (b) diverge from each other, to facilitate the engagement of a rope between the jaws.

In use, a rope is slipped between the jaws 10(a) and (b) of both pairs of jaws 10 and is gripped firmly therebetween by means of the springs 40. The jaws are adapted to firmly contact the rope to achieve an electrical connection therewith, but not so tightly as to immobilize the rope and prevent it from sliding through the jaws. The jaws permit the rope to be pulled through the device, as seen in FIG. 1, to provide a continuous measurement of the conductivity of the entire length of rope. As the rope is pulled through the device, the measuring circuit assesses the conductivity of the segment of rope within the probe means. The various indicator means signal the user whether the portion of rope under test adheres to an acceptable predetermined conductivity level.

Figure 13:
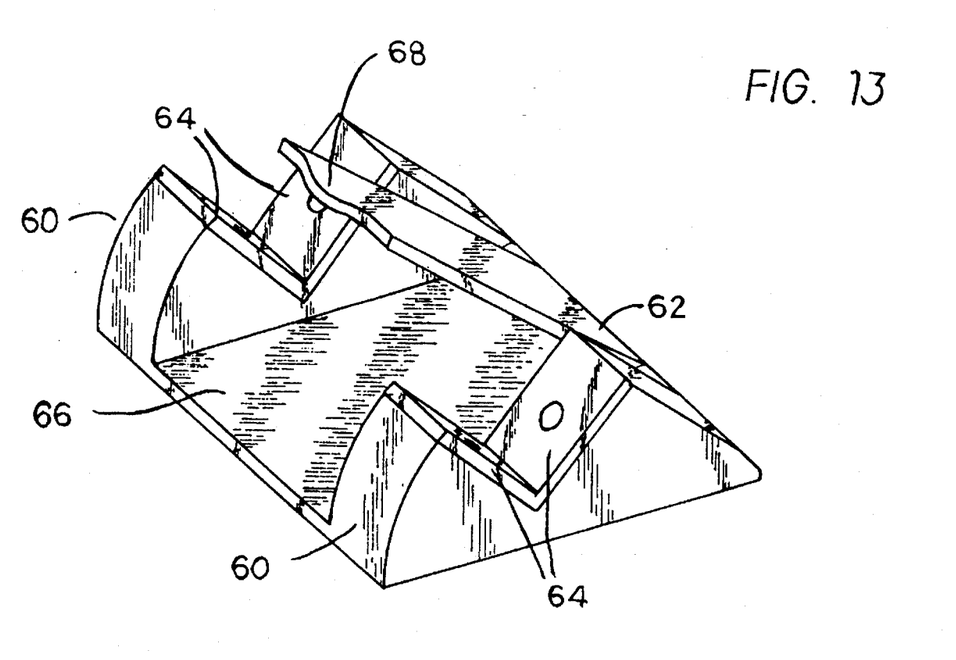
FIG. 13 is a perspective view of the probe means portion of a second embodiment of the device.

In a second embodiment, the probe portion of the device, seen in FIG. 13, comprises a pair of spaced-apart rope contact members 60, with a single spring-biased retention member 62 positioned generally midway between the contact members. The contact members each comprise a V-shaped steel shoe 64 mounted to a holder 66, in turn mounted to the upper face of the base, not shown. The retention member 62 comprises a flat plate hinged to the holder 66 and spring-biased towards the contact members. A small tongue 68 extends outwardly from the end of the retention member to aid in placing the rope within the probe. The shoes 64 are each linked to the testing circuit as shown in FIG. 2.

Figure 14:
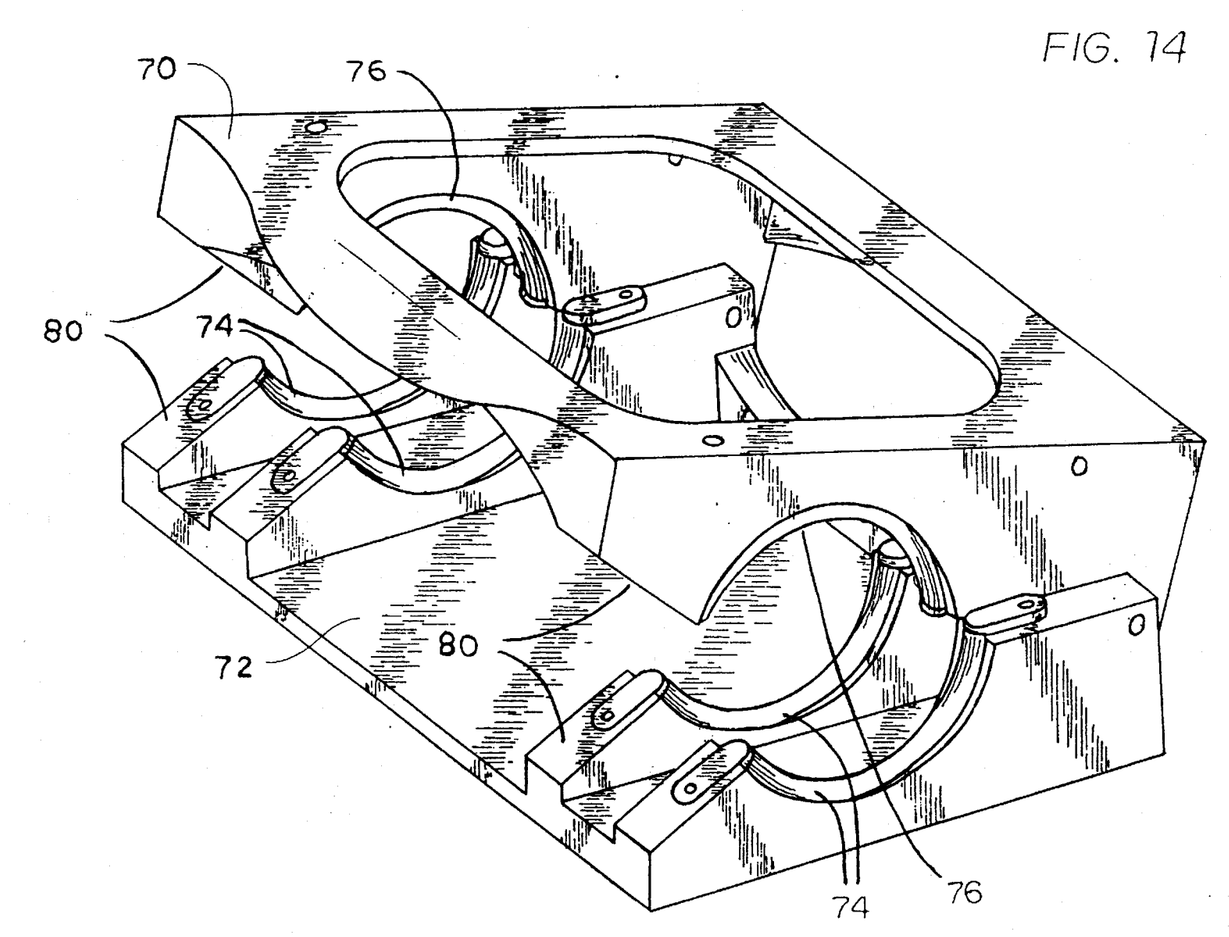
FIG. 14 is a perspective view of the probe means portion of a third embodiment of the device.

In a third embodiment, the probe portion of the device, seen in FIG. 14, is similar to that of the first embodiment, but comprises rope retention and contact members incorporated into upper and lower holders 70 and 72, respectively, that are hinged together adjacent an edge thereof. The lower holder 72 is mounted to the upper face of the base, not shown, and the upper and lower holders are spring-biased towards each other. Rope contact members each comprise two pairs of concavely-curving lower shoes 74 mounted to two corresponding members of the lower holder 72, with one of the shoes being electrically connected to the electrical circuit, not shown. Rope retention members each comprise a single concavely-curving upper shoe 76 mounted to the upper holder 70, with the shoes of each retainer being each positioned generally midway between a corresponding pair of lower shoes 74. The upper shoes 76 may also be linked to the testing circuit. The upper and lower holders and the shoes mounted thereto terminate at their openable ends in an outwardly-diverging portion 80 that facilitates the insertion of a segment of rope under test between the contact and retention members. The upper and lower holders interleave together when they are folded together, in a fashion similar to that of the first embodiment.

Figure 15:
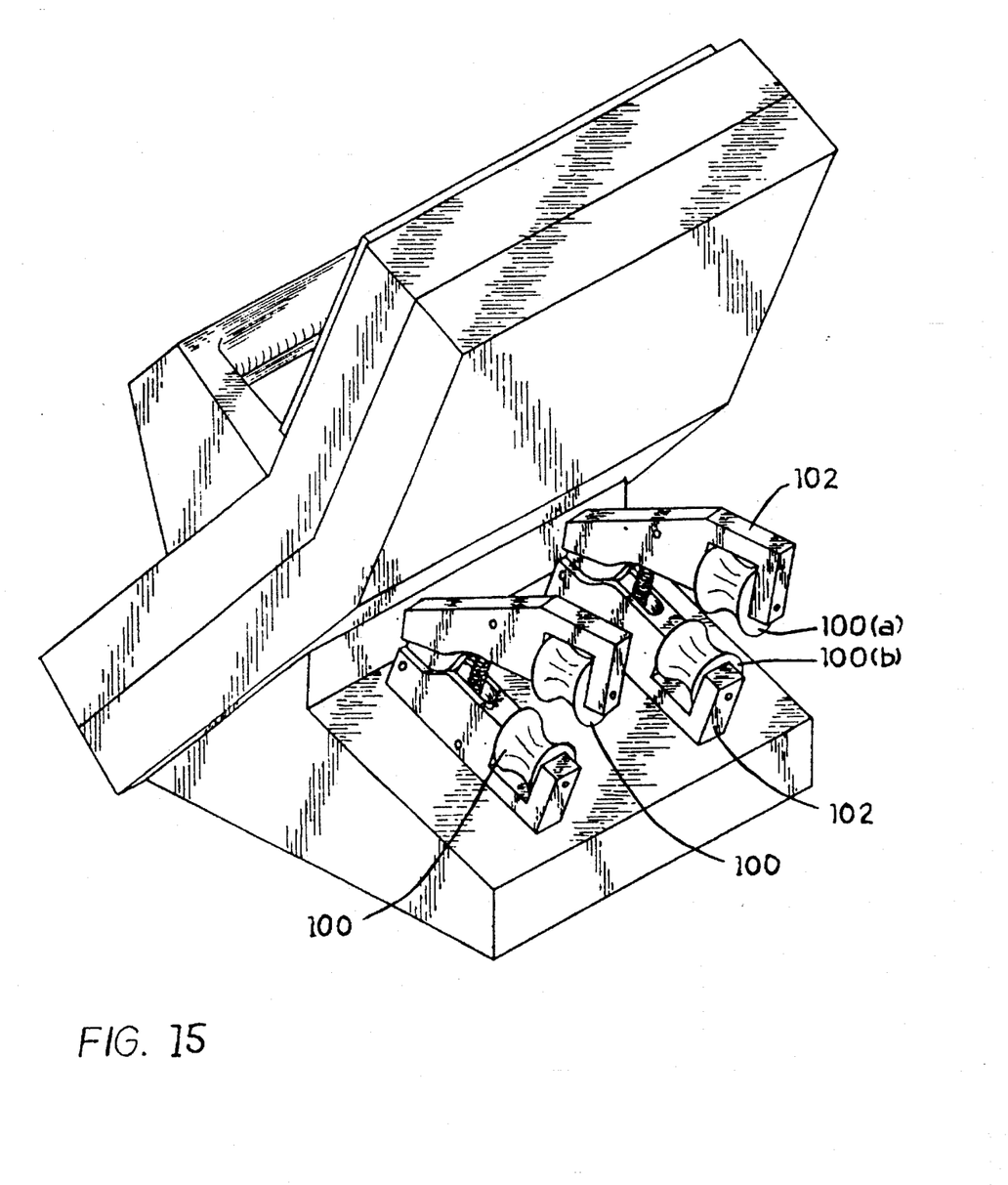
FIG. 15 is a fourth embodiment of the device.

A fourth embodiment of the device, seen in FIG. 15, encompasses the use of spaced-apart sets of rollers as the contact and retainer members. The rollers 100 are rotatably mounted on opposing jaw members 102, that are spring-biased towards each other in the same manner as the first embodiment. The rollers comprise upper and lower rollers 100(*a*) and (*b*), that comprise contact and retainer members, respectively. The rollers have an hourglass shape to maximize the rope contact area. As in the other embodiments, the contact and retainer members may be both connected to the testing circuit.

Figure 16:
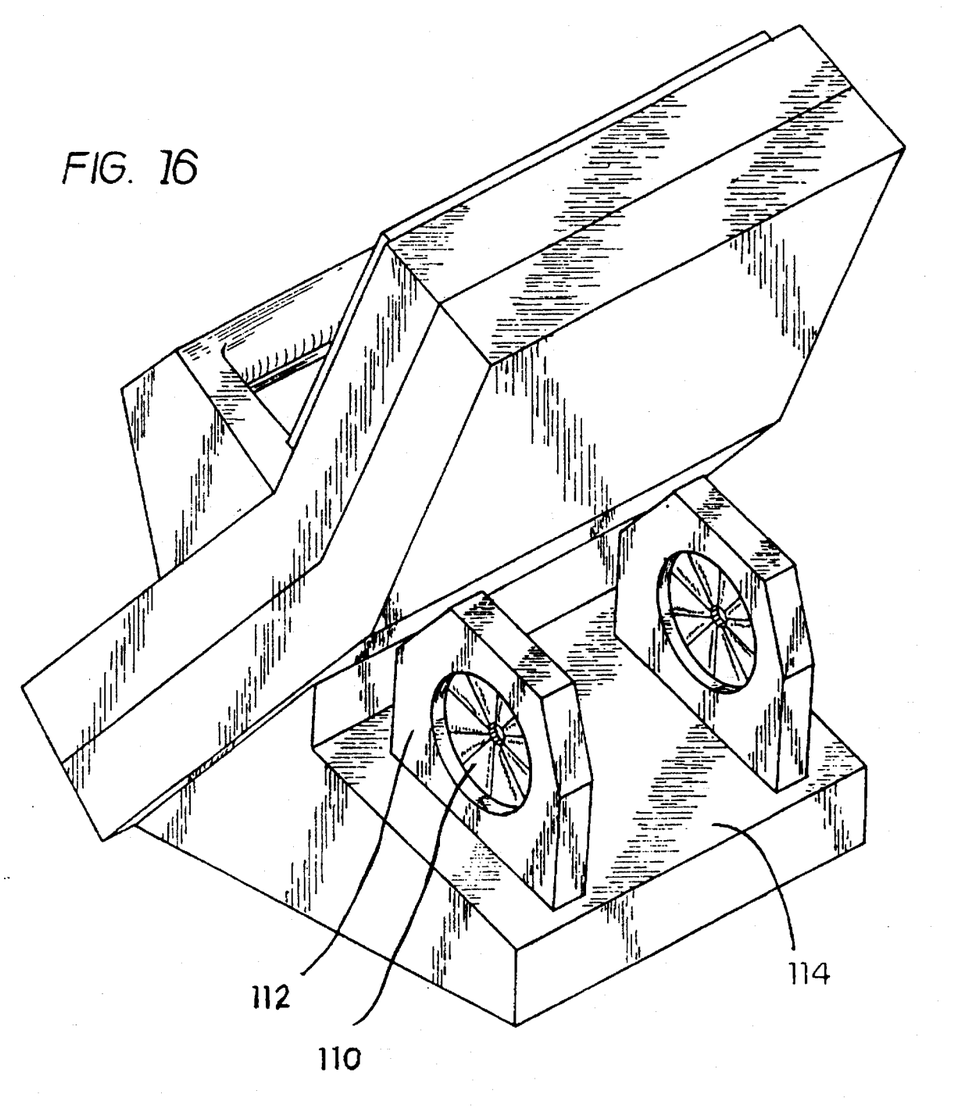
FIG. 16 is a fifth embodiment of the device.

A fifth embodiment of the device employs two spaced-apart sliding contact and retainer members each incorporated within an iris-type member. The contact and retainer members comprise an array of flexible leaves 110 extending inwardly from an annular retainer 112 and adapted to press against a rope inserted through the retainer. The retainer is mounted to the base 114 of the device. The leaves 110 are electrically conductive and may be fabricated from a metal-impregnated plastic. Some, and preferably all, of the leaves are connected to the testing circuit.

Although the present invention has been described by way of preferred embodiments thereof, it will be obvious to one skilled in the art that the invention may encompass numerous departures from and variations of these embodiments, without departing from the spirit and scope of the invention as defined in the appended claims.

We claim:

1. A tester for measuring the dielectric integrity of a rope, said tester comprising:
   a) a base;
   b) first and second rope contact members mounted to said base and spaced apart from each other, said rope contact members adapted to contact the surface of a rope under test to make electrical contact with a segment of said rope at opposing ends of said segment;
   c) at least one rope retention member comprising a member spring-biased towards at least one of said rope contact members when said rope is placed between said rope retention member and said rope contact members;
   d) an electrical circuit comprising: a power source electrically linked to a first of said rope contact members and adapted to generate a potential difference between said rope contact members; a metering circuit adapted to measure electrical conductivity or resistivity axially along said segment, said metering circuit being electrically linked to a second of said rope contact members and to said power source; and indicator means to indicate the conductivity or resistivity of said rope segment under test.

2. A device as claimed in claim 1, wherein said rope contact members and said rope retention member are provided with sliding engagement means to slideably engage a rope placed therebetween.

3. A device as claimed in claim 2, wherein said sliding engagement means includes an indentation recessed into a face of each of said rope contact members, adapted to slideably retain a rope placed therein.

4. A device as claimed in claim 2, wherein said sliding engagement means includes an indentation recessed into a face of said rope retention member, adapted to slideably retain a rope placed therein.

5. A device as claimed in claim 2, wherein said sliding engagement means comprises a roller member incorporated within said rope contact member or said rope retention member, adapted to engage a rope placed within said device.

6. A rope tester as claimed in claim 2, wherein said sliding engagement means comprises an iris having flexible leaves extending inwardly from an annular member.

7. A device as claimed in claim 1 wherein said electrical circuit further comprises a transformer circuit linked to said power source and adapted to boost the voltage within said circuit to between 9,000 and 11,000 volts, with said rope contact members being positioned generally four inches apart on said base.

8. A device as claimed in claim 1, wherein one of said rope retention members is provided, positioned generally midway between said rope contact members.

9. A device as claimed in claim 8, wherein said rope retention member comprises an elongate plate having a generally flat surface facing said rope contact members, said rope contact members each having an indentation recessed into a surface thereof generally facing said rope retention member, said indentation adapted to cooperate with said rope retention member to slideably retain said rope between said rope contact members and said rope retention member.

10. A device as claimed in claim 1, wherein said rope contact members each comprise a pair of shoes having a concave face, said shoes being mounted within a retainer, with said retainer being mounted to said base.

11. A device as claimed in claim 10, wherein said retainer comprises upper and lower parts hinged together and spring-biased towards each other, with said lower part housing said rope contact members and said upper part housing said rope retainer member, said rope retainer comprising a shoe mounted to said upper part.

12. A rope tester as claimed in claim 1, wherein said indicator means comprises a light adapted to indicate when the conductivity of a rope being tested by said device exceeds a predetermined limit.

13. A rope tester as claimed in claim 1, wherein said indicator means comprises a sound-generating means adapted to produce an audible signal when the conductivity of a segment of rope being tested by said device exceeds a predetermined limit.

14. A rope tester as claimed in claim 1, wherein said indicator means comprises a pivoting needle-type current meter display.

* * * * *